United States Patent [19]

Pellicciari et al.

[11] Patent Number: 5,424,292
[45] Date of Patent: Jun. 13, 1995

[54] 5-AMINOSALICYLIC ACID DERIVATIVES FOR THE THERAPY OF CHRONIC INFLAMMATORY BOWEL DISEASES

[75] Inventors: Roberto Pellicciari; Aaron Garzon; Carlo Clerici; Camillo M. F. G. Palazzi, all of Segrate, Italy

[73] Assignee: Depha Team s.r.l., Segrate, Italy

[21] Appl. No.: 984,575

[22] PCT Filed: Sep. 10, 1991

[86] PCT No.: PCT/EP91/01718
§ 371 Date: Mar. 3, 1993
§ 102(e) Date: Mar. 3, 1993

[87] PCT Pub. No.: WO92/04369
PCT Pub. Date: Mar. 19, 1992

[30] Foreign Application Priority Data

Sep. 12, 1990 [IT] Italy ................... 21443/90

[51] Int. Cl.$^6$ .................. C07K 5/10; C07K 5/08; C07K 5/06; A61K 38/06
[52] U.S. Cl. ........................ 514/19; 514/18; 530/331; 530/330
[58] Field of Search ........... 530/331, 330; 514/19, 514/18

[56] References Cited

U.S. PATENT DOCUMENTS 4,505,898 3/1985 Marks et al. ................ 514/18
5,120,306 6/1992 Gosselin ..................... 604/51

FOREIGN PATENT DOCUMENTS 536278 of 0000 Switzerland .
555805 of 0000 Switzerland .
81/02672 of 0000 WIPO .
86/03199 of 0000 WIPO .

Primary Examiner—Jill Warden
Assistant Examiner—Carol Salata
Attorney, Agent, or Firm—Griffin, Butler, Whisenhunt & Kurtossy

[57] ABSTRACT

5-Aminosalicylic acid derivatives acylated at the amino group with glutamic or aspartic acid and/or having the carboxy group involved in a peptide bond with the leucyl-prolyl residue are useful as pro-drugs of 5-aminosalicylic acid.

4 Claims, No Drawings

5-AMINOSALICYLIC ACID DERIVATIVES FOR THE THERAPY OF CHRONIC INFLAMMATORY BOWEL DISEASES

The invention refers to 5-aminosalicylic acid (5-ASA) derivatives of general formula 1

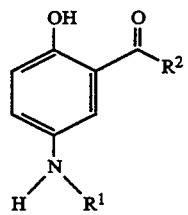

wherein $R_1$ is hydrogen, glutamyl (Glu) or aspartyl (Asp) and $R_2$ is OH or the residue leucyl-prolyl, with the proviso that $R_1$ and $R_2$ cannot be contemporaneously hydrogen and hydroxy, respectively.

The present invention also relates to a process for the preparation of compounds of formula 1.

The compounds of the invention of the general formula 1 have therefore the following formulae:

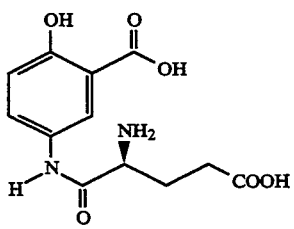

($R^1$ = Glu and $R^2$ = OH)

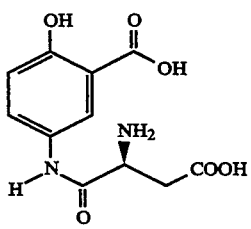

($R^1$ = Asp and $R^2$ = OH)

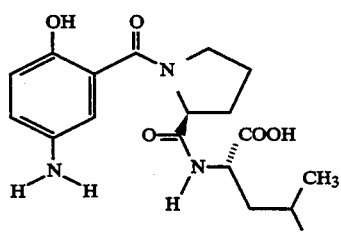

($R^1$ = H and $R^2$ = Pro—Leu)

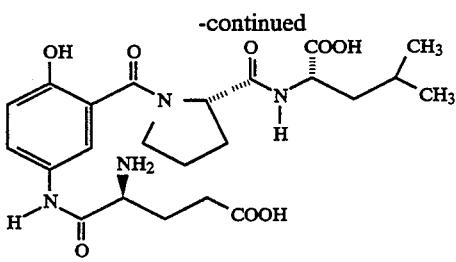

($R^1$ = Glu and $R^2$ = Pro—Leu)

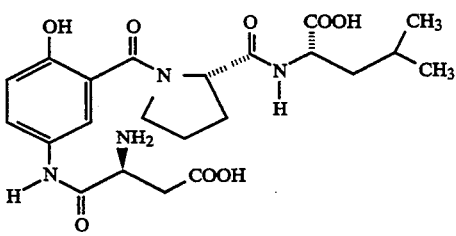

($R^1$ = Asp and $R^2$ = Pro—Leu)

The invention refers also to the non-toxic salts of the above compounds, to pharmaceutical compositions containing them and to processes for the preparation thereof.

Said compounds are useful in chronic inflammatory bowel diseases, thanks to their topical antiinflammatory effect on intestinal mucosa portions affected by the lesions.

This activity involves interactions with specific peptidases present on the brush border of small intestine, which can hydrolize selectively the amino acidic residues, releasing in situ the active principle 5-ASA. It is in fact known that some chronic inflammatory diseases, such as Chron's disease and ulcerative rectocolitis, are since many years treated with drugs able to inhibit the arachidonic acid derivatives biosynthesis, such as $PGE_2$, leucotrienes and thromboxane $B_2$. Sulfasalazine, of formula 7, was one of the first drugs used; it is metabolized to 5-ASA and sulfapyridine by reductive cleavage of the azide bond by intestinal bacteria.[1,2]

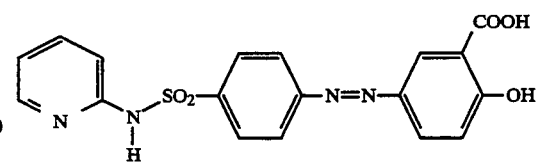

The properties of sulfasalazine seem to be non-therapeutic against Crohn's disease and of ulcerative rectocolitis. Moreover, sulfasalazine is responsible in some patients of the following side-effects:
- nausea and anorexia (dose-related)
- cutaneous rash and hematic dyscrasia (hydiosyncrasic phenomena)
- decrease of the number and of the motility of spermatozoa.

All the above effects are mainly due to sulfapyridine and in about 10% of the patients were so serious as to ask for the drop out of the treatment.[3]

Moreover 5-ASA, the active part of the sulfasalazine molecule, is not stable at the gastric pH and it is rapidly absorbed in the small intestine. This prevents its use as such by the oral use, unless at high doses.

The compounds of general formula 1, having specific amino acidic residues bound to the 1-carboxy and/or 5-amino substituents of the corresponding 5-ASA, are hydrolized in vivo at the level of brush border of the ileum where specific aminopeptidases are present (Aminopeptidases A) [5-7,8,12] which are able to hydrolize selectively an N-terminal amidic bond when a Glu or Asp residue is bound to that position. Moreover, dipeptides containing amino acids Glu or Asp as terminal residues are known to be resistant to pancreatic peptidases, [5-7,8-10] important requisite for the non-occurrence of the fast 5-ASA release. Finally, always in the brush border, a second class of peptidases is present, namely the carboxypeptidases, which are able to selectively hydrolize a C-terminal amide bond between an amino acid and a penultimate Pro residue. [1-3,4-6]

Thanks to these characteristics the compounds of the invention may then undergo a chemoselective enzymatic hydrolysis so as to release 5-ASA directly at the distal intestine.

The compounds of the invention are easily prepared in liquid phase by means of usual methods for the peptide synthesis, starting from 5-aminosalicylic acid which is suitably protected and then reacted with an N-protected glutamic or aspartic acid derivatives and/or with a suitably protected leucyl-prolyl derivative. The removal of the protecting groups yields the desired compounds.

A general synthesis scheme is hereinbelow reported and the experimental conditions used for the preparation of the compounds 2, 3, 4, 5, 6 are described.

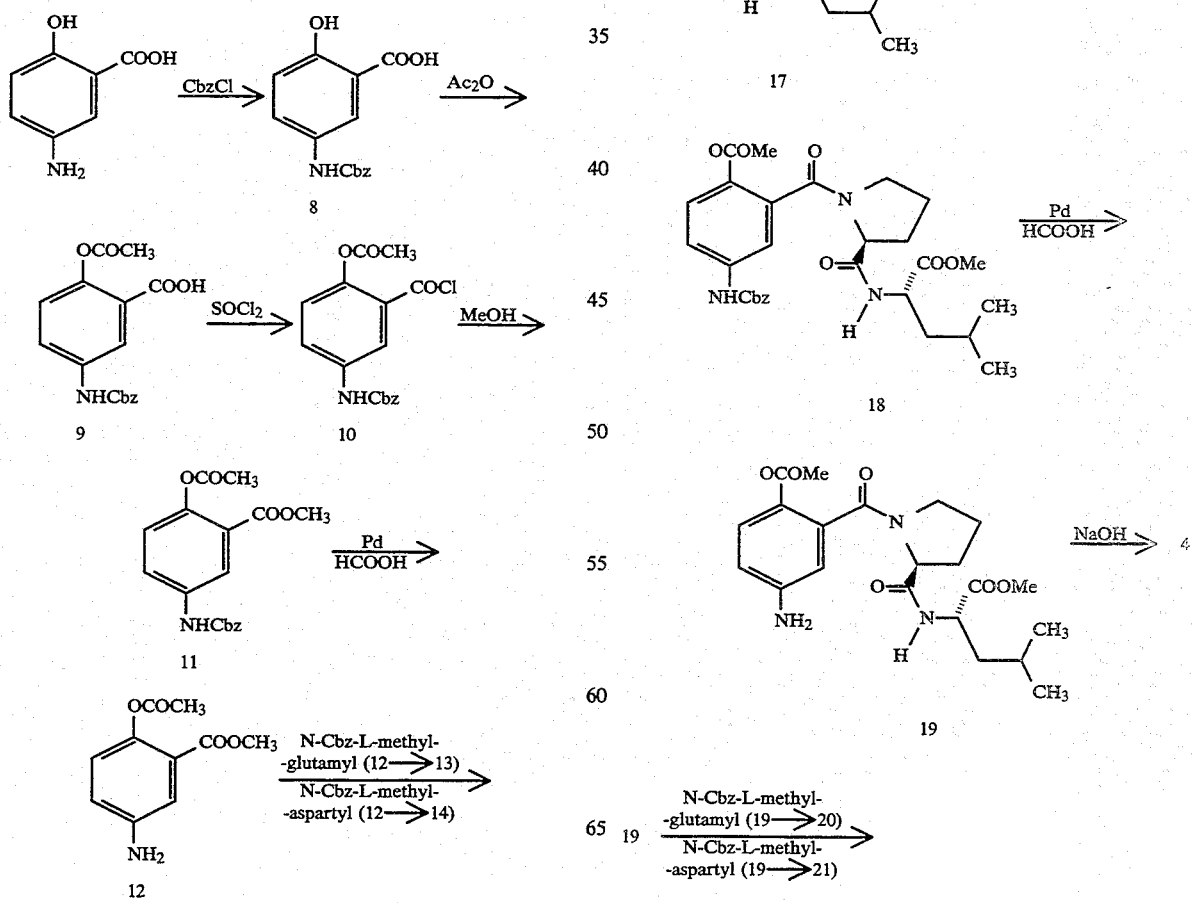

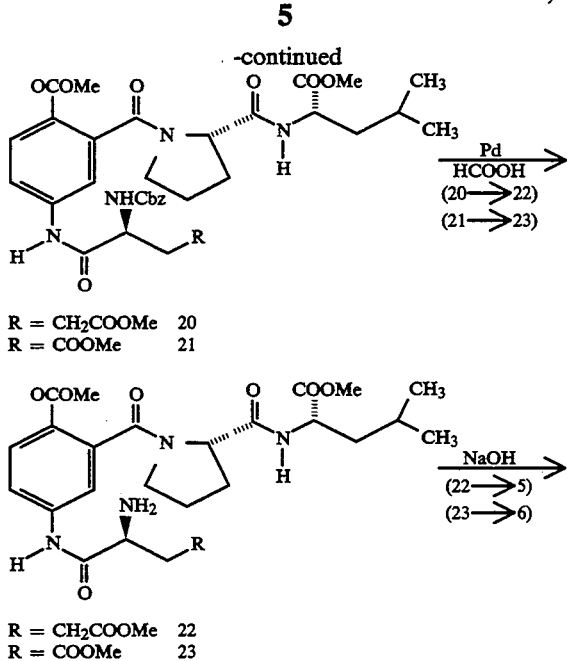

R = CH₂COOMe  20
R = COOMe  21

R = CH₂COOMe  22
R = COOMe  23

R = CH₂COOH  5
R = COOH  6

5-(N-benzyloxycarbonyl)-aminosalicylic acid 8

5-aminosalicylic acid (30 g, 0.20 tool) was suspended into a saturated NaHCO₃ solution (500 ml). Solid NaHCO₃ (10 g) was then added to the suspension at 0° C. under stirring and then benzylchloroformate (36.7 g, 0.215 tool) was added dropwise.

An abundant precipitate of the desired product was formed when the reaction was over and it was filtered. The filtrate was washed with ethyl ether (2×100 ml), the aqueous phase was acidified with 10% HCl and extracted with ethyl acetate (3×100 ml). The pooled organic extracts were dried on anhydrous sodium sulphate, evaporated under vacuum to give, together with the previously separated precipitate, 53 g of 8 (yield 92%).

¹H-NMR (DMSO-d₆):
ppm 5.17 (s, 2H, -CH₂Ph); 7.00—8.05 (m, 8H, H-aromatic);
9.8 (s, 1H, COOH).

5- (N-benzyloxycarbonyl)-amino-2-acetylsalicylic acid 9

Pyridine ( 1.39 ml) and acetic anhydride (35.5 g, 0.34 tool ) were added to a stirred suspension of the compound 8 in acetic acid (280 ml). After 2 hours the formed precipitate was filtered and dried under vacuum. 40.1 g of 9 were obtained (yield 70%).

¹-NMR (MeOH-d₄):
ppm 2.15 (s, 3H, -CO-CH₃); 5.10 (s, 2H, -CH₂Ph); 6.90–8.00 (m, 8H, H-aromatic).

5-(N-benzylcarbonyl)-amino-2-acetylsalicyl chloride 10

A suspension of 9 (35 g, 0.106 mol), thionyl chloride (25.2 g, 0.21 mol), pyridine (20 ml) in anhydrous benzene (150 ml), kept under stirring and in nitrogen atmosphere, was refluxed for 3 hours. The resulting clear solution was cooled to obtain a white precipitate that was filtered and dried under vacuum to obtain 29.89 g of 10 (81% yield).

5-(N-benzyloxycarbonyl) amino-2-acetylsalicyl methyl ester 11

A suspension of 10 (10 g, 28.8 mmol) in methanol (100 ml) is kept under magnetic stirring until complete dissolution (about 2 hours). The resulting solution is evaporated under vacuum to give about 9.53 g of 11 (97% yield) .

¹-NMR (CDCl₃):
ppm 2.2 (s, 3H, -CO-CH₃); 3.8 (s, 3H, COOCH₃); 5.10 (s, 2H, -CH₂Ph); 6.8-7.9 (m, 8H, H-aromatic).

5-amino-2-acetylsalicyl methyl ester 12

A solution of 11 (7 g, 20.4 mmol ) in methanol (100 ml) and formic acid (10 ml) is poured into column containing Palladium Black. The obtained eluate is evaporated under reduced pressure. The residue is crystallized from ethyl acetate/n-hexane to give 3.58 g of 12 (yield 84%).

¹H-NMR (CDCl₃):
ppm 2.25 (s, 3H, -CO-CH₃); 3.7 (s, 3H, COOCH₃); 7.3–7.8 (m, 3H, H-aromatic ) .

5-(N-benzyloxycarbonyl-L-methylglutamyl)-amino-2-acetylsalicyl methyl ester 13
5-(N-benzyloxycarbonyl-L-methylaspartyl)-amino-2acetylsalicyl methyl ester 14

A solution of N-benzyloxycarbonyl-5-L-methylglutamyl)-(2.12 g, 7.18 mmol) or of N-benzyloxycarbonyl-4-L-methylaspartyl (2.01 g, 7.18 mmol) in anhydrous methylene chloride (10 ml) , kept at −10° C. under magnetic stirring and argon atmosphere, is added with N-methylmorpholine (1 ml, 7.9 mmol), then with isobutyl chloroformate (1 ml, 7.18 mmol) . The reaction mixture is left to react for 30 minutes, then it is filtered and the filtrate is combined with a solution of 12 (7.15 mmol) in anhydrous methylene chloride (40 ml). After that, the reaction mixture is kept under magnetic stirring and argon atmosphere for 4 hours, then it is evaporated and the residue is chromatographed through silica gel column (d.- 6 cm, h.- 20 cm), eluting first with chloroform (500 ml) , then with 99:1 chloroform/methanol. 3.04 g of 13 (87% yield) or 2.88 g of 14 (85% yield) are obtained.

¹H-NMR (CDCl₃) of 13:
ppm 2.2 (s, 3H, -CO-CH₃); 2.36 (m, 4H, -CH₂-CH₂-); 3.7 (s, 3H, COOCH₃); 3.73 (s, 3H, COOCH₃); 4.35 (m, 1H, -CH-NH-); 5.15 (s, 2h, -CH₂Ph); 6.2 (d, 1H, NH); 7.15–8.05 (s, 3H, H-aromatic).

¹-NMR (CDCl₃) of 14:
ppm 2.22 (s, 3H, -CO-CH₃); 2.33 (m, 2H, -CH₂-; 3.7 (s, 3H, COOCH₃); 3.70 (s, 3H, COOCH₃); 4.30 (m, 1H, -CH-NH-); 5.15 (s, 2h, -CH₂Ph); 6.2 (d, 1H, NH); 7.15–8.05 (s, 3H, H-aromatic)..

5- (N-L-methylglutamyl)-amino-2-acetylsalicyl methyl ester 15

5-(N-L-methylaspartyl)-amino-2-acetylsalicyl methyl ester 16

A solution of 13 (5 g, 10.29 mmol) or 14 (4.85 g, 10.29 mmol) in methanol (50 ml) and formic acid (5 ml) is poured into a column containing Palladium Black. The obtained eluate is evaporated under reduced pressure, then the residue is crystallized from ethyl acetate/n-hexane to give 3.44 g of 15 (95% yield) or 3.34 g of 16 (96% yield).

(N-L-glutamyl)-amino-2-salicylic acid 2

(N-L-aspartyl)-amino-2-salicylic acid 3

A solution of 15 (2 g, 5.68 mmol) or 16 (1.91 g, 5.68 mmol) in 2N NaOH (50 ml) is kept under magnetic stirring for 6 hours at room temperature. Then the mixture is acidified with 10% HCl to form a precipitate which is filtered and dried under vacuum, to give 1.5 g of 2 (94% yield) or 1.46 g of 3 (96% yield).

$^1$H-NMR (CDCl$_3$) of 2:

ppm 2.35. (m, 4H, -CH$_2$-CH$_2$-); 4.30 (m, 1H, -CH-NH-); 6.1 (d, 1H, NH); 7.2–8.05 (m, 3H, H-aromatic).

$^1$-NMR CDCl$_3$ of 3:

ppm 2.30 (m, 2H, -CH$_2$-); 4.35 (m, 1H, -CH-NH-); 6.1 (d, 1H, NH); 7.2–8.05 (m, 3H, H-aromatic).

5-(N-benzyloxycarbonyl-amino-2-acetylsalicyl L-proline-L-leucine-O-methyl 18

A solution of 10 (28 g, 0.08 tool) and 17 (19.4 g, 0.08 tool) in anhydrous carbon tetrachloride (300 ml), kept under magnetic stirring and nitrogen atmosphere, is refluxed for 12 hours. Then the reaction mixture is filtered and the filtrate is evaporated under reduced pressure. The residue is chromatographed on silica gel (d. - 5 cm, h. - 20 cm), eluting with chloroform to obtain 25 g of the tripeptide 18 (57% yield).

$^1$-NMR (CDCl$_3$):

ppm 0.95 (2d, 6H, -CH(CH$_3$)$_2$); 1.5–2.15 (m, 10H, -CO-CH$_3$, -CH$_2$-CH, -CH$_2$-CH$_2$-CH-CO); 3.15 (s, 3H, COOMe); 3.7 (m, 2H, -CH$_2$-N-CO); 4.2–4.7 (m, 2H, -CH-CO, -NH-CH-COOMe); 5.1 (d, 2H, CH$_2$Ph); 6.9–8.0 (m, 8H, H-aromatic).

5-amino-2-acetylsalicyl L-proline-L-leucine-O-methyl 19

A solution of 18 (17 g, 0.03 mol) in methanol (110 ml) and formic acid (11 ml) is poured into a column containing Palladium Black. The obtained eluate is evaporated under reduced pressure, then the residue is dissolved with a NaHCO$_3$ saturated solution (100 ml) and extracted with ethyl acetate. The combined organic extracts are dried over anhydrous sodium sulphate and evaporated under vacuum, to give 10 g of 19 (80% yield).

$^1$H-NMR (CDCl$_3$):

ppm 0.95 (2d, 6H, -CH(CH$_3$)$_2$); 1.6–2.35 (m, 10H, -CO-CH$_3$, -CH$_2$-CH, -CH$_2$-CH$_2$-CH-CO); 3.6–4.8 (m 7H, COOMe, -CH$_2$-N-CO, -CH-CO, -NH-CH-COOMe); 6.85 (m, 3H, H-aromatic).

5-aminosalicyl L-proline-L-leucine 4

A solution of 19 (5 g, 0.012 mmol) in 2N NaOH (50 ml) is kept under magnetic stirring for 6 hours at room temperature, then the reaction mixture is neutralized with 10% HCl to form a precipitate which is then filtered and dried under vacuum to obtain 4.09 g of 4 (94% yield).

$^1$-NMR (CDCl$_3$):

ppm 0.95 (2d, 6H, -CH(CH$_3$)$_2$); 1.6–2.30 (m, 7H, -CH$_2$-CH, -CH$_2$-CH$_2$-CH-CO); 4.2 (m, 4H, -NH-CH-COOH, -CH$_2$-N-CO, -CH-CO); 6.80–7.20 (m, 3H, H-aromatic).

5-[N-(N'-benzyloxycarbonyl)-5'-methyl-L-glutamyl]-amino-2-acetylsalicyl L-proline-L-leucine-O-methyl 20

5-[N-(N'-benzyloxycarbonyl)-4'-methyl-L-aspartyl]-amino-2-acetylsalicyl L-proline-L-leucine-O-methyl 21

A solution of N-benzyloxycarbonyl-5-L-methylglutamyl (2.12 g, 7.18 mmol) or of N-benzyloxycarbonyl-4-L-methylaspartyl (2.01 g, 7.18 mmol) in anhydrous methylene chloride (10 ml), kept at −10° C. under magnetic stirring and argon atmosphere, is added with N-methylmorpholine (1 ml, 7.9 mmol), then with isobutyl chloroformate (1 ml, 7.18 mmol). The reaction mixture is left to react for 30 minutes, then it is filtered and the filtrate is combined with a solution of tripeptide 19 (3 g, 7.15 mmol) in anhydrous methylene chloride (8 ml). The reaction mixture is kept under magnetic stirring and argon atmosphere for 4 hours, then it is evaporated and the residue is chromatographed through silica gel column (d.- 3 cm, h.- 20 cm), eluting first with chloroform (500 ml), then with 99:1 chloroform/methanol. 3 g of tripeptide 20 (60% yield) or 3.18 g of 21 (65% yield) are obtained.

$^1$-NMR (CDCl$_3$) of 20:

ppm 0.85 (2d, 6H, -CH(CH$_3$)$_2$); 1.35–2.50 (m, 14H, -CO-CH$_3$, -CO-(CH$_2$)$_2$-CH, -CH$_2$-CH, -CO-CH-CH$_2$-CH$_2$-); 3.5–4.1 (m, 8H, COOMe, COOMe, -CH$_2$-N-CO); 4.15-4.75 (m, 3H, -CO-CH-NHCbz, -NH-CH-COOMe, -N-CH-CO); 5.1 (s, 2H, -CH$_2$Ph); 6.2–7.8 (s, 8H, H-aromatic).

$^1$-NMR (CDCl$_3$) of 21:

ppm 0.80 (2d, 6H, -CH(CH$_3$)$_2$); 1.35–2.50 (m, 12H, -CO-CH$_3$, -CO-CH$_2$-CH, -CH$_2$-CH, -CO-CH-CH$_2$-CH$_2$-); 3.55–4.15 (m, 8H, COOMe, COOMe, -CH$_2$-N-CO); 4.15–4.80 (m, 3H, -CO-CH-NHCbz, -NH-CH-COOMe, -N-CH-CO); 5.15 (s, 2H, -CH$_2$Ph); 6.2–7.8 (s, 8H, H-aromatic).

5-(N-5'-methyl-L-glutamyl)-amino-2-acetylsalicyl L-proline-L-leucine-O-methyl 22

5-(N-4'-methyl-L-aspartyl)-amino-2-acetylsalicyl L-proline-L-leucine-O-methyl 23

A solution of 20 (3 g, 4.31 mmol) or 21 (2.93 g, 4.31 mmol) in methanol (50 ml) and formic acid (50 ml) is poured into a column containing Palladium Black. The obtained eluate is evaporated under reduced pressure, then the residue is dissolved with a NaHCO$_3$ saturated solution (50 ml) and extracted with ethyl acetate (4×20 ml). The combined organic extracts are dried over anhydrous sodium sulphate and evaporated under vacuum, to give 2.13 g of tripeptide 22 (88% yield) or 2.13 g of 23 (90% yield).

$^1$LH-NMR (CDCl$_3$) of 22:

ppm 0.85 (2d, 6H, -CH(CH$_3$)$_2$); 1.37–2.40 (m, 14H, -CO-CH$_3$, -CO-(CH$_2$)$_2$-CH, -CH$_2$-CH, -CH$_2$-CH$_2$-CH-CO); 3.5–4.1 (m, 8H, COOMe, COOMe, -CH$_2$-N-CO); 4.15–4.70 (m, 3H, -N-CH-CO, -NH-CH-COOMe, -CO-CH-NH$_2$); 7.1–7.7 (s, 3H, H-aromatic).

$^1$-NMR (CDCl$_3$) of 23:

ppm 0.87 (2d, 6H, -CH(CH$_3$)$_2$); 1.30–2.45 (m, 12H, -CO-CH$_3$, -CO-CH$_2$-CH, -CH$_2$-CH, -CH$_2$-CH$_2$-CH-CO); 3.5–4.15 (m, 8H, COOMe, COOMe, -CH$_2$-N-CO); 4.20–4.75 (m, 3H, -N-CH-CO, -NH-CH-COOMe, -CO-CH-NH$_2$); 7.1–7.7 (s, 3H, H-aromatic).

5-(N-L-glutamyl)-aminosalicyl L-proline-L-leucine 5

5-(N-L-aspartyl)-aminosalicyl L-proline-L-leucine 6

A solution of 22 (2 g, 3.56 mmol) or 23 (1.95 g, 3.56 mmol ) in 2N NaOH (30 ml) is kept under magnetic stirring for 6 hours at room temperature, then the reaction mixture is neutralized with 10% HCl and cooled to obtain a precipitate which is filtered and dried under vacuum to give 1.75 g of 5 (99% yield) or 1.62 g of 6 (95% yield).

$^1$H-NMR (CDCl$_3$) of 5:

ppm 0.85 (2d, 6H, -CH(CH$_3$)$_2$); 1.37–2.30 (m, 11H, -CO-(CH$_2$)$_2$-CH, -CH$_2$-CH, -CH$_2$-CH$_2$-CH-CO); 3.8 (m, 2H, -CH$_2$-N-CO); 4.15–4.70 (m, 3H, -N-CH-CO, -CH-COOH, -CO-CH-NH$_2$); 7.1–7.6 (m, 3H, H-aromatic ).

$^1$-NMR (CDCl$_3$) of 6:

ppm 0.85 (2d, 6H, -CH(CH$_3$)$_2$); 1.35–2.35 (m, 9H, -CO-CH$_2$-CH, -CH$_2$-CH, -CH$_2$-CH$_2$-CH-CO); 3.83 (m, 2H, -CH$_2$-N-CO) 4.13–4.75 (m, 3H, -N-CH-CO, -CH-COOH, -CO-CH-NH$_2$); 7.1–7.6 (m, 3H, H-aromatic).

The best pharmacokinetic characteristics of the compounds of the present invention can be evidenced analyzing the recovery urines and feces of 5-ASA and N-acetyl-5-ASA, compared with 5-ASA as such and sulfasalazine.

Particularly, male Fischer rats weighing about 200–250 g were used.

Part of the animals were subjected to outer colostomy. After general anaesthesia by means of pentobarbital (Nembutal 7.5 rag/100 g body weight) administered intraperitoneally, a median laparatomy was effected, then ascending colon was sectioned and connected to the outer abdominal wall, followed by suture of the incision.

After about 7 days, which were required to restore the intestinal function, 5-ASA, sulfasalazine and derivatives 2, 3, 4, 5 and 6 were administered at doses equivalent to 60 mg/kg of 5-ASA through a metal probe inserted into stomach.

The same administration was carried out also in animals which had not been subjected to surgery.

The rats were then placed in metabolic cages, from which feces and urine were withdrawn at 2 hour intervals for 48 hours.

The test results are summarized in the following table.

|  | Urine | Feces |
|---|---|---|
| 5-ASA | 79 ± 3% | 05 ± 3% |
| Sulfasalazine | 30 ± 7% | 37 ± 4% |
| Compound 2 | 34 ± 4% | 45 ± 4% |
| Compound 3 | 33 ± 3% | 46 ± 3% |
| Compound 4 | 53 ± 3% | 25 ± 4% |
| Compound 5 | 15 ± 6% | 54 ± 9% |
| Compound 6 | 14 ± 4% | 54 ± 3% |
| Recovery percentages of 5-ASA + N-acetyl-5-ASA in feces and urine by HPLC | | |

The study evidences that the compounds of the present invention are particularly active when compared with sulfasalazine and 5-ASA.

Therefore, the compounds of the invention can conveniently be used as active ingredients of pharmaceutical compositions for the treatment of chronic inflammatory bowel diseases such as Crohn's disease and ulcerous rectocolitis, since they have a topical anti-inflammatory activity on the injured tracts of intestinal mucosa.

Examples of said pharmaceutical compositions for the oral administration comprise capsules, pearls, tablets, sachets, containing 200 to 1,000 mg of the active ingredient per unitary.-dose, to be administered two/-three times daily, according to the disease to be treated and the conditions of the patient.

Pharmaceutical compositions for the rectal administration are suppositories containing 200 to 1,000 mg of the active ingredient per unitary dose, to be administered two/three times daily, and clysters, containing 2 to 10 g of the active ingredient per unitary dose, to be administered one/two times daily, according to the disease to be treated and the conditions of the patient.

The compositions of the invention may contain other active ingredients having a complementary or anyhow useful activity.

REFERENCES

1) M. A. Peppercorn and P. Goldman; J. Pharm. Exp. Terap.; 1972,181,555.

2) K. M. Das, M. A. Eastwood, J. P. McManus and W. Sircos; Scand. J. Gastroen.; 1974,9,137.

3) K. M. Das, M. A. Eastwood, J. P. McManus and W. Sircus; Eng. J. Med.; 1973,289,491.

4) M. A. Peppercorn and P. Goldman; Gastroen.; 1973,64,240.

5) S. Auricchio, L. Greco, B. De Vizia and V. Buonocore; Gastroen.; 1978,75,1073.

6) S. Auricchio; "Text book of gastroenterology and nutrition in infancy", Raven Press, N.Y., 1981, pp 375.

7) S. Auricchio, A. Stellato and B. De Vizia; Pediatr. Res.; 1981,15,991.

8) H. Skovbjerg; Clin. Chim. Acta; 1981,112,205.

9) H. Skovbjerg, O. Noren and H. Sjostrom; Scand. J. Clin. Lab. Invest.; 1978,38,723.

10) M. Triadou, J. Bataille and J. Schmitz; Gastroen.; 1983,85,1326.

11) E. E. Sterchi, J. R. Green and M. J. Lentze; Biochem. Soc. Trans.; 1981,9,130.

12) N. Tobey, W. Heizer, R. Yeh, T. Huang and C. Hoffner; Gastroen.; 1985,88,923.

We claim:

1. Compounds of the formula 1

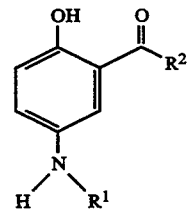

wherein R$_1$ is hydrogen, glutamyl (Glu) or aspartyl (Asp) and R$_2$ is OH or the residue leucyl-prolyl, with the proviso that R$_1$ and R$_2$ cannot be contemporaneously hydrogen and hydroxy, respectively.

2. A compound according to claim 1 having the following formulas 2–6.

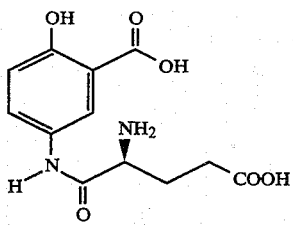

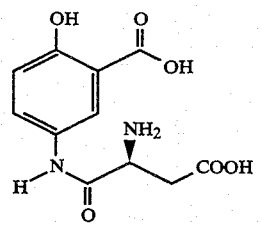

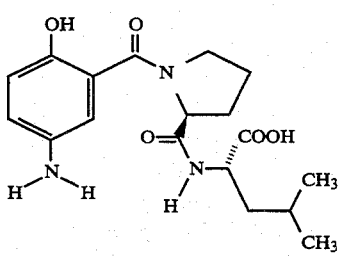

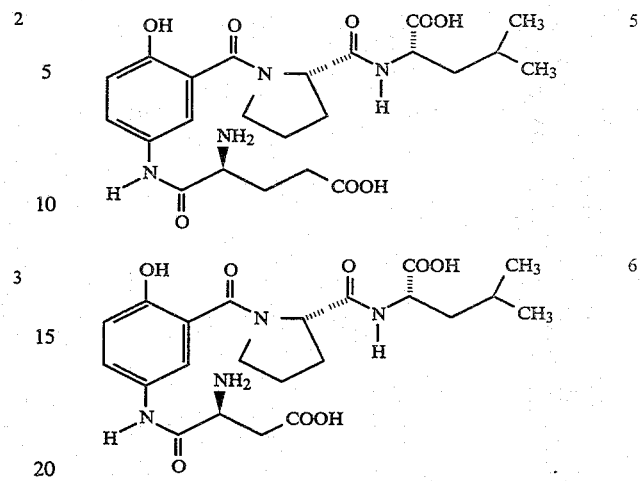

3. Pharmaceutical compositions containing as the active ingredient a compound of claim 1 in admixture with a pharmaceutically acceptable carrier.

4. A method for treatment of an animal suffering from a chronic inflammatory bowel disease of chronic intestinal inflammation, Crohn's disease or ulcerative colitis, comprising administering to the animal an anti-inflammatory effective amount of at least one of the compounds of claim 1.

* * * * *